US012590918B2

(12) United States Patent
Choa et al.

(10) Patent No.: US 12,590,918 B2
(45) Date of Patent: Mar. 31, 2026

(54) CAPACITIVE GAS SENSOR AND METHOD FOR MANUFACTURING SAME

(71) Applicant: Industry-University Cooperation Foundation Hanyang University Erica Campus, Ansan-si (KR)

(72) Inventors: Yong Ho Choa, Seongnam-si (KR); Ji Young Park, Ansan-si (KR); Min Seob Lim, Seoul (KR); Hong Baek Cho, Ansan-si (KR); Han Seung Lee, Ansan-si (KR)

(73) Assignee: Industry-University Cooperation Foundation Hanyang University Erica Campus, Ansan-si (KR)

( * ) Notice: Subject to any disclaimer, the term of this patent is extended or adjusted under 35 U.S.C. 154(b) by 310 days.

(21) Appl. No.: 18/192,899

(22) Filed: Mar. 30, 2023

(65) Prior Publication Data

US 2023/0236144 A1 Jul. 27, 2023

Related U.S. Application Data

(63) Continuation of application No. PCT/KR2021/016893, filed on Nov. 17, 2021.

(30) Foreign Application Priority Data

Nov. 25, 2020 (KR) ........................ 10-2020-0160431

(51) Int. Cl.
*G01N 27/22* (2006.01)
*G01N 33/00* (2006.01)

(52) U.S. Cl.
CPC ........... *G01N 27/22* (2013.01); *G01N 27/221* (2013.01); *G01N 27/227* (2013.01); *G01N 33/00* (2013.01); *G01N 33/0036* (2013.01); *G01N 2027/222* (2013.01)

(58) Field of Classification Search
CPC .... G01N 27/22; G01N 27/221; G01N 27/227; G01N 33/00; G01N 33/0036
See application file for complete search history.

(56) References Cited

U.S. PATENT DOCUMENTS

| | | | | |
|---|---|---|---|---|
| 4,892,834 A | * | 1/1990 | Rauh ..................... | G01N 27/227 73/31.06 |
| 9,304,102 B2 | | 4/2016 | Day et al. | |

(Continued)

FOREIGN PATENT DOCUMENTS

| | | | | |
|---|---|---|---|---|
| CN | 108226236 A | * | 6/2018 | ........... G01N 27/223 |
| JP | H8-010202 B2 | | 1/1996 | |

(Continued)

OTHER PUBLICATIONS

Translation of CN108226236.*

(Continued)

*Primary Examiner* — Helen C Kwok

(74) *Attorney, Agent, or Firm* — Finch & Maloney PLLC

(57) ABSTRACT

Provided is a capacitive gas sensor. The capacitive gas sensor comprises a sensitive material for adsorbing and desorbing a target gas, an upper electrode surrounding the sensitive material, a lower electrode facing the upper electrode, and a porous structure disposed between the upper electrode and the lower electrode, wherein the capacitance of the sensitive material changes as the sensitive material adsorbs and desorbs the target gas.

8 Claims, 20 Drawing Sheets

(56)                References Cited

U.S. PATENT DOCUMENTS

| | | |
|---|---|---|
| 11,059,559 B2 | 7/2021 | Cedar et al. |
| 2010/0148222 A1* | 6/2010 | Krauss ............... G01N 27/4141 |
| | | 977/773 |
| 2016/0061761 A1* | 3/2016 | Shim .................... G01N 27/122 |
| | | 436/151 |
| 2018/0045663 A1* | 2/2018 | Ahn ................... G01N 33/0031 |
| 2018/0202961 A1* | 7/2018 | Sussner ................. A61B 5/055 |
| 2019/0204265 A1* | 7/2019 | Stowell ............. B01J 20/28066 |
| 2019/0250117 A1* | 8/2019 | Itoh ........................ G01N 27/22 |
| 2019/0391103 A1* | 12/2019 | Durupt ................ G01N 27/223 |
| 2020/0018720 A1* | 1/2020 | Mochizuki ......... G01N 33/0009 |
| 2024/0361235 A1* | 10/2024 | Choa ..................... G01N 21/33 |

FOREIGN PATENT DOCUMENTS

| | | |
|---|---|---|
| JP | 2019-152511 A | 9/2019 |
| KR | 10-1025715 B1 | 4/2011 |
| KR | 10-1201896 B1 | 11/2012 |
| KR | 10-2016-0001369 A | 1/2016 |
| KR | 10-2018-0107491 A | 10/2018 |
| KR | 10-2168091 B1 | 10/2020 |

OTHER PUBLICATIONS

Kim et al., "High-selectivity Eco-friendly Hydrophilic Gas Sensor Using the Functional Groups of Graphene Oxide Coated on an Aluminum Oxide Nanostructure", 2017 IEEE Sensors (DOI: 10.1109/ICSENS.2017.8234361) (2017).

Zamani et al., "Capacitive-type gas sensors combining silicon semiconductor and NaNo. 2-based solid electrolyte for NO2 detection", Sensors and Actuators B 109, pp. 300-306 (2005).

International Search Report and Written Opinion of the International Searching Authority mailed Mar. 4, 2022 for International Application No. PCT/KR2021/016893, 5 pages.

* cited by examiner

Fig.1

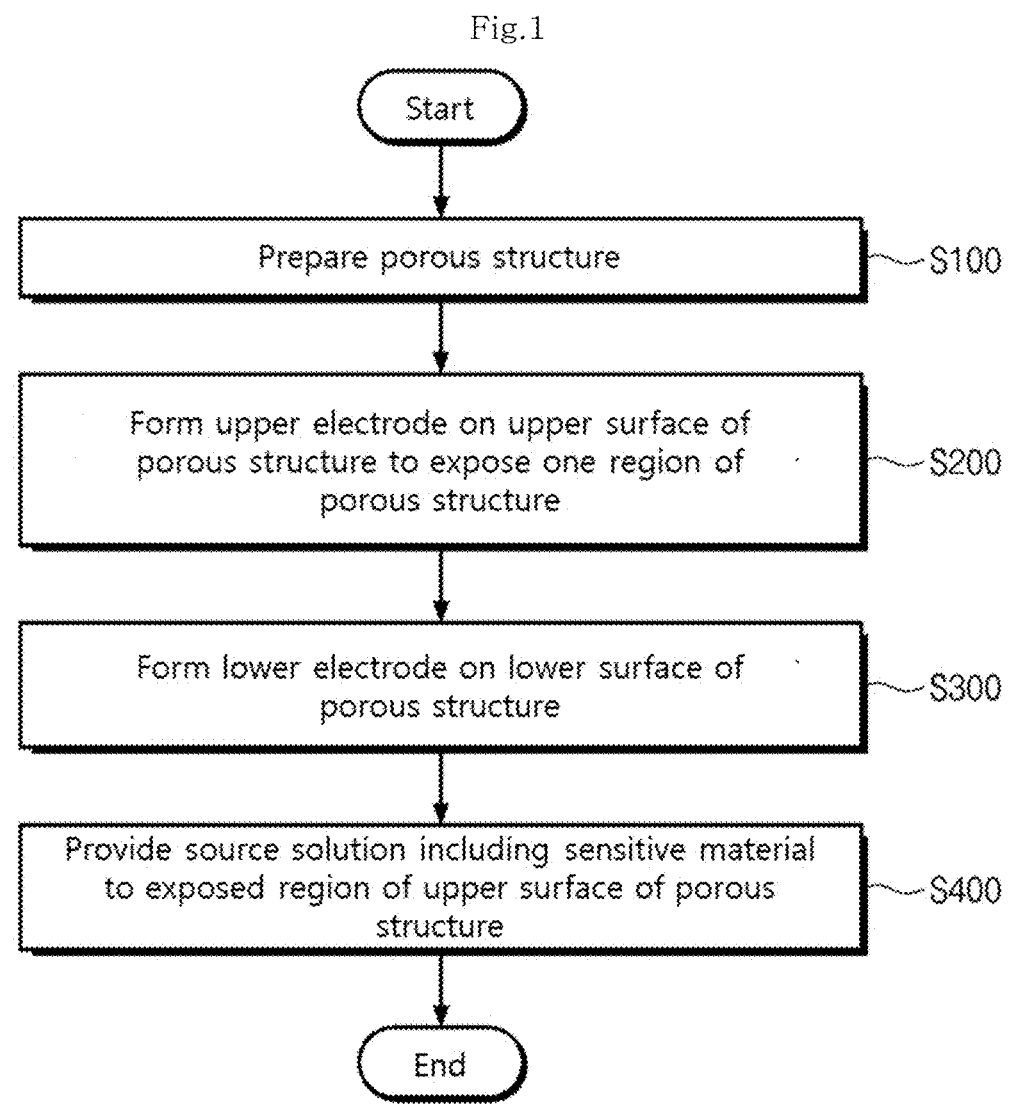

Start

↓

| Prepare porous structure | ~S100 |

↓

| Form upper electrode on upper surface of porous structure to expose one region of porous structure | ~S200 |

↓

| Form lower electrode on lower surface of porous structure | ~S300 |

↓

| Provide source solution including sensitive material to exposed region of upper surface of porous structure | ~S400 |

↓

End

CAPACITIVE GAS SENSOR AND METHOD FOR MANUFACTURING SAME

CROSS REFERENCE TO RELATED APPLICATIONS

This is a continuation of PCT/KR2021/016893 (filed 17 Nov. 2021), which claims the benefit of Republic of Korea Patent Application KR 10-2020-0160431 (filed 25 Nov. 2020). The entire disclosure of both of these priority applications is hereby incorporated by reference herein.

TECHNICAL FIELD

The present invention relates to a capacitive gas sensor and a method for manufacturing the same, and more specifically, to a capacitive gas sensor that adsorbs or desorbs a target gas by a sensitive material, and a method for manufacturing the same.

BACKGROUND ART

Recently, as an interest in environmental pollution and health increases, the necessity for sensing various harmful gases is greatly increased. Gas sensors are in a high demand due to needs for the overall industrial structure such as health, environment, agriculture, and national defense. Therefore, the gas sensor becomes an essential means for realization of a future society for improvement of a human living environment, and more accurate measurement and control of environmentally harmful gases are required.

In order for such a gas sensor to be put to practical use, the gas sensor needs to have characteristics of high sensitivity, high selectivity, long-term stability, and high response, and requires low power consumption and integration. In order to meet these requirements, research on gas sensor development using structures and materials of various sensors is being conducted. A resistive gas sensor using an oxide semiconductor such as tin oxide (SnO2), tungsten oxide (WO3), zinc oxide (ZnO), or the like, may obtain high sensitivity, but has problems of instability of contact resistance, difficulty in sensing selectivity to other kinds of gases, deterioration of long-term stability, and an increase in power consumption of the sensor itself because a heater is essential due to operation at a high temperature.

Accordingly, various technologies for a capacitive gas sensor different from a resistive gas sensor have been developed. For example, Korean Patent Registration No. 10-1201896 (Application No.: 10-2009-0025688, Applicant: Electronics and Telecommunications Research Institute) discloses a capacitive-type harmful environmental gas sensor including: an insulating substrate; a metal electrode and a micro-thin film heater heating line which are integrally coplanar with the insulating substrate; and an oxide sensing layer that is formed by being coated on the metal electrode and the micro-thin film heater heating wire and including a nanocrystal composite oxide thin film or composite oxide nanofibers in which a p-type oxide semiconductor and an n-type oxide semiconductor are mixed.

DISCLOSURE

Technical Problem

One technical problem to be solved by the present invention is to provide a capacitive gas sensor that can be driven at room temperature, and a method for manufacturing the same.

Another technical problem to be solved by the present invention is to provide a capacitive gas sensor with improved response speed and recovery speed, and a method for manufacturing the same.

Still another technical problem to be solved by the present invention is to provide a capacitive gas sensor that selectively senses any one of a methanol gas, a toluene gas, and an acetone gas, and a method for manufacturing the same.

Still another technical problem to be solved by the present invention is to provide a capacitive gas sensor with reduced noise due to a phase difference, and a method for manufacturing the same.

The technical problems to be solved by the present invention are not limited to those described above.

Technical Solution

In order to solve the above-described technical problems, the present invention provides a capacitive gas sensor. According to one embodiment, a capacitive gas sensor may include: a sensitive material for adsorbing or desorbing a target gas; an upper electrode surrounding the sensitive material; a lower electrode facing the upper electrode; and a porous structure disposed between the upper electrode and the lower electrode, wherein a capacitance of the sensitive material changes the sensitive material adsorbs or desorbs the target gas.

According to one embodiment, a frequency of a voltage applied to the upper electrode and the lower electrode is differently controlled according to a type of the target gas.

According to one embodiment, the target gas may include any one of a methanol gas, a toluene gas, and an acetone gas, and any one of the methanol gas, the toluene gas, and the acetone gas may be selectively sensed according to the frequency of the voltage applied to the upper electrode and the lower electrode.

According to one embodiment, the capacitive gas sensor may sense the methanol gas when the frequency of the voltage applied to the upper electrode and the lower electrode is 10 KHz or greater and 1 MHz or less.

According to one embodiment, the capacitive gas sensor may sense the toluene gas when the frequency of the voltage applied to the upper electrode and the lower electrode is greater than 800 Hz and less than 3,000 Hz.

According to one embodiment, the capacitive gas sensor may sense the acetone sensor when the frequency of the voltage applied to the upper electrode and the lower electrode is greater than 300 Hz and less than 800 Hz.

According to one embodiment, the porous structure may include any one of anodic aluminum oxide (AAO), silicon oxide ($SiO_2$), polyimide (PI), polyethylene terephthalate (PET), polyethylene naphthalate (PEN), and polytetrafluoroethylene (PTFE).

According to one embodiment, the sensitive material may include any one of graphene, carbon nanotube (CNT), amorphous carbon, active carbon, and biochar.

According to one embodiment, the sensitive material may include a functional group including a carboxyl group (—COOH) and a hydroxyl group (—OH), and the target gas may be adsorbed or desorbed by the functional group.

According to one embodiment, the upper electrode may have a ring shape with a hollow formed at a central portion thereof, and the lower electrode may have a circle plate shape.

According to one embodiment, the capacitive gas sensor may include sensitive material that is disposed in the hollow formed at the central portion of the upper electrode.

In order to solve the above-described technical problems, the present invention provides a method for manufacturing a capacitive gas sensor.

According to one embodiment, a method for manufacturing a capacitive gas sensor may include: preparing a porous structure; forming an upper electrode on an upper surface of the porous structure to expose one region of the upper surface of the porous structure; forming a lower electrode on a lower surface of the porous structure; and providing a source solution including a sensitive material to an exposed region of the upper surface of the porous structure.

According to one embodiment, the providing of the source solution including the sensitive material may include: preparing the source solution in which the sensitive material is mixed with a solvent; and providing the source solution to the exposed region of the upper surface of the porous structure while the porous structure is being heat-treated.

Advantageous Effects

According to one embodiment of the present invention, a capacitive gas sensor may include: a sensitive material for adsorbing or desorbing a target gas (for example, a volatile organic compounds gas such as a methanol gas, a toluene gas, and an acetone gas); an upper electrode surrounding the sensitive material; a lower electrode facing the upper electrode; and a porous structure (for example, anodic aluminum oxide) disposed between the upper electrode and the lower electrode, wherein a capacitance of the capacitive gas sensor changes as the sensitive material adsorbs or desorbs the target gas. Accordingly, it is possible to provide a capacitive gas sensor with improved response speed and recovery speed.

In addition, the capacitive gas sensor may selectively sense any one of a methanol gas, a toluene gas, and an acetone gas according to a frequency of a voltage applied to the upper electrode and the lower electrode.

In addition, the upper electrode of the capacitive gas sensor may have a ring shape, and the lower electrode of the capacitive gas sensor may have a circle plate shape. Accordingly, noise due to a phase difference is reduced, so that sensing sensitivity is improved and the capacitive gas sensor can be easily driven at room temperature.

Furthermore, as the capacitive gas sensor can be driven at room temperature, miniaturization thereof can be facilitated and power consumption can be efficiently reduced.

DESCRIPTION OF DRAWINGS

FIG. 1 is a flowchart showing a method for manufacturing a capacitive gas sensor according to an embodiment of the present invention.

FIG. 16 is a graph showing a comparison between sensing characteristics for a type of a target gas of the capacitive gas sensor according to the embodiment of the present invention.

FIG. 17 is a graph showing sensitivity according to concentrations of gases provided to the capacitive gas sensor according to the embodiment of the present invention.

MODE FOR INVENTION

Figure 2:
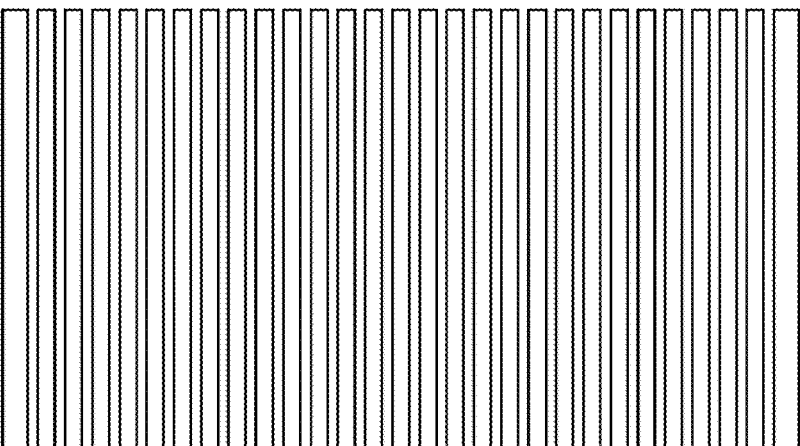
FIG. 2 is a view showing a porous structure included in the capacitive gas sensor according to the embodiment of the present invention.

Hereinafter, preferred embodiments of the present invention will be described in detail with reference to the accompanying drawings. However, the present invention may be embodied in different forms and should not be construed as limited to the embodiments set forth herein. Rather, the embodiments are provided so that this disclosure will be thorough and complete, and will fully convey the scope of the present invention to those skilled in the art.

In the present specification, it will be understood that when an element is referred to as being "on" another element, it can be formed directly on the other element or intervening elements may be present. In the drawings, the thicknesses of layers and regions are exaggerated for clarity.

It will be also understood that although the terms first, second, third etc. may be used herein to describe various elements, these elements should not be limited by these terms. These terms are only used to distinguish one element from another element. Thus, a first element in some embodiments could be termed a second element in other embodiments without departing from the teachings of the present invention. Embodiments explained and illustrated herein include their complementary counterparts. As used herein, the term "and/or" includes any and all combinations of one or more of the associated listed elements.

The singular expression also includes the plural meaning as long as it does not differently mean in the context. In addition, the terms "comprise", "have" etc., of the description are used to indicate that there are features, numbers, steps, elements, or a combination thereof, and they should not exclude the possibilities of combination or addition of one or more features, numbers, operations, elements, or a combination thereof. Furthermore, it will be understood that when an element is referred to as being "connected" or "coupled" to another element, it may be directly connected or coupled to the other element or intervening elements may be present.

In addition, when detailed descriptions on related known functions or constitutions are considered to unnecessarily cloud the gist of the present invention in describing the present invention below, the detailed descriptions will not be included.

Figure 3:
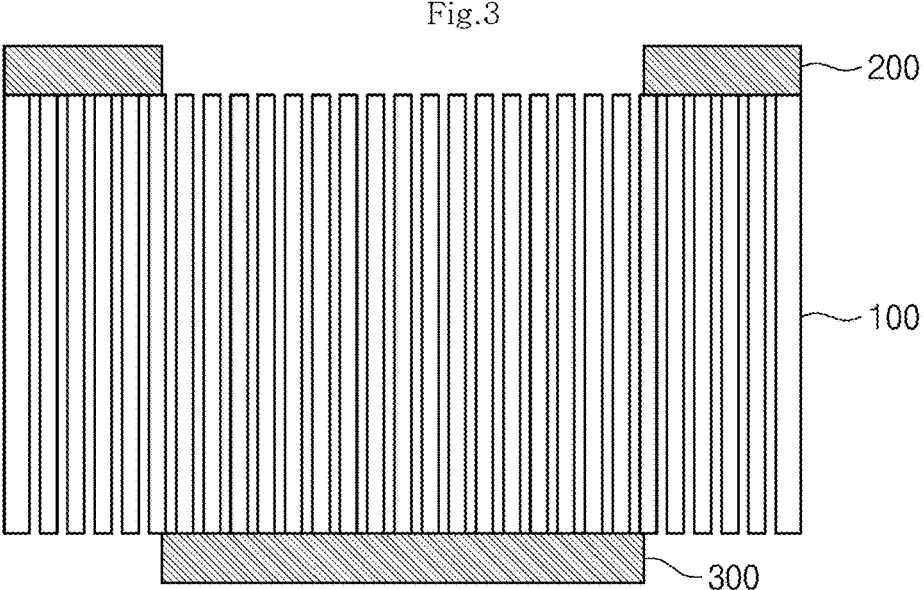
FIG. 3 is a view showing a step of forming an upper electrode and a lower electrode in the method for manufacturing a capacitive gas sensor according to the embodiment of the present invention.
Figure 4:
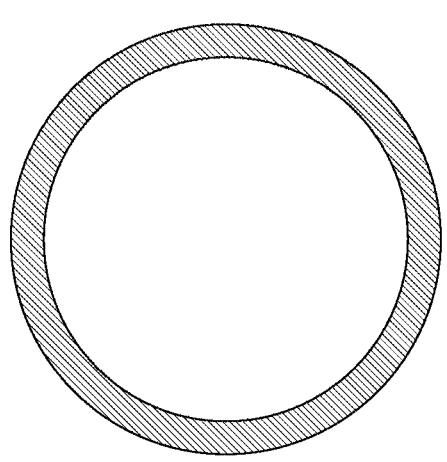
FIG. 4 is a view showing the upper electrode and the lower electrode included in the capacitive gas sensor according to the embodiment of the present invention.
Figure 4:
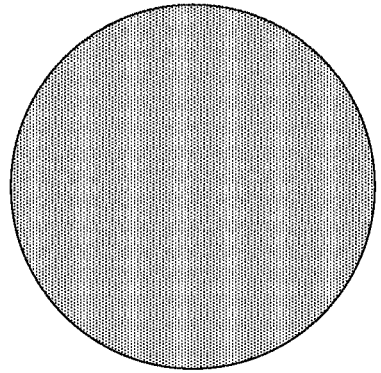
Figure 5:
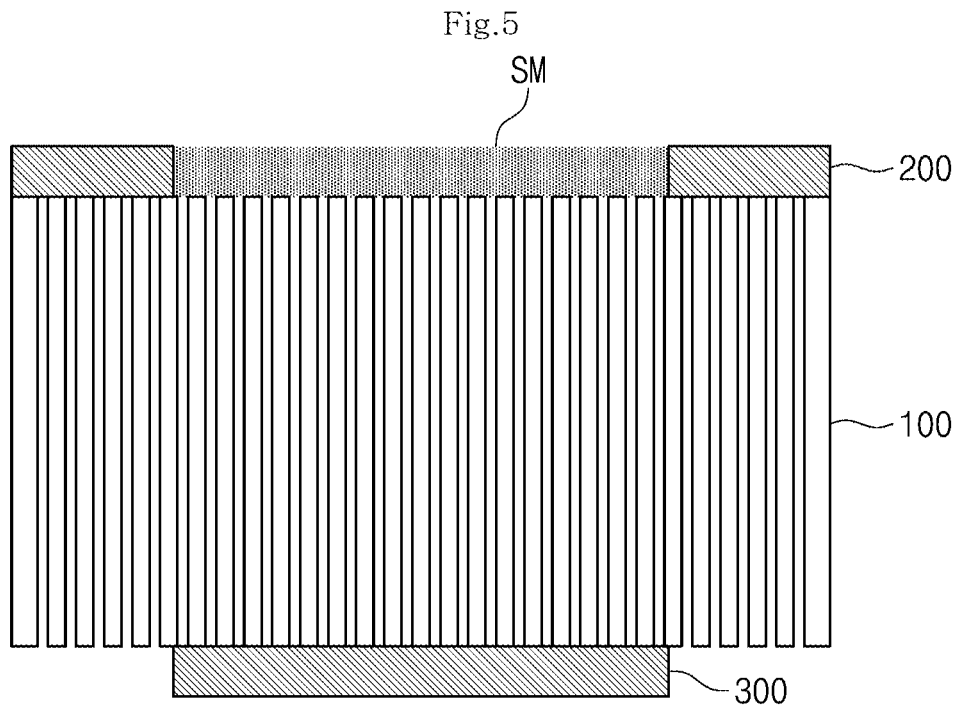
FIG. 5 is a view showing a step of providing a source solution in the method for manufacturing a capacitive gas sensor according to the embodiment of the present invention.

FIG. 1 is a flowchart showing a method for manufacturing a capacitive gas sensor according to an embodiment of the present invention, FIG. 2 is a view showing a porous structure included in the capacitive gas sensor according to the embodiment of the present invention, FIG. 3 is a view showing a step of forming an upper electrode and a lower electrode in the method for manufacturing a capacitive gas sensor according to the embodiment of the present invention, FIG. 4 is a view showing the upper electrode and the lower electrode included in the capacitive gas sensor according to the embodiment of the present invention, FIG. 5 is a view showing a step of providing a source solution in the method for manufacturing a capacitive gas sensor according to the embodiment of the present invention.

Referring to FIGS. 1 to 5, a porous structure 100 may be prepared (S100). According to one embodiment, the porous structure 100 may include any one of anodic aluminum oxide (AAO), silicon oxide ($SiO_2$), polyimide (PI), polyethylene terephthalate (PET), polyethylene naphthalate (PEN), and polytetrafluoroethylene (PTFE). Hereinafter, in describing the capacitive gas sensor according to the embodiment of the present invention, a case in which the porous structure 100 is anodic aluminum oxide will be exemplarily described.

An upper electrode 200 may be formed on an upper surface of the porous structure 100 (S200). The upper electrode 200 may include a metal. For example, the metal may include gold (Au).

According to one embodiment, the upper electrode 200 may expose one region of the upper surface of the porous structure. For example, the upper electrode 200 may have a ring shape with a hollow formed at a central portion thereof. In this case, one region of the upper surface of the upper electrode 200 may be exposed through the hollow formed at the central portion of the upper electrode 200.

A lower electrode 300 may be formed on a lower surface of the porous structure 100 (S300). The lower electrode 300 may include a metal. For example, the metal may include gold (Au). According to one embodiment, the lower electrode 300 may have a shape different from that of the upper electrode 200. For example, the lower electrode 300 may have a circle plate shape.

As described above, when the upper electrode 200 has a ring shape and the lower electrode 300 has a circle plate shape, the capacitive gas sensor to be described below may reduce noise due to a phase difference, thereby improving sensing sensitivity and being easily driven at room temperature.

A source solution including a sensitive material SM may be provided to the exposed region of the upper surface of the porous structure 100 (S400). Accordingly, the capacitive gas sensor according to the embodiment may be manufactured.

According to one embodiment, the providing of the source solution including the sensitive material SM may include: preparing the source solution in which the sensitive material SM is mixed with a solvent; and providing the source solution to the exposed region of the upper surface of the porous structure 100 while the porous structure 100 is being heat-treated. Since the source solution is provided while the porous structure 100 is being heat-treated, the solvent in the source solution may be evaporated. Accordingly, the sensitive material SM may remain on the upper surface of the porous structure 100.

The sensitive material SM may adsorb or desorb a target gas. According to one embodiment, the target gas may include any one of a methanol gas, a toluene gas, and an acetone gas. According to another embodiment, the target gas may be a volatile organic compounds (VOCs) gas.

According to one embodiment, the sensitive material SM may include any one of graphene, carbon nanotube (CNT), amorphous carbon, active carbon, and biochar. When the graphene is used as the sensitive material SM, the graphene may have a relatively high surface area due to the two-dimensional characteristics of the graphene. Accordingly, an adsorption area of the target gas is relatively increased, and thus sensing characteristics of a gas sensor, which will be described below, may be improved.

In addition, the sensitive material SM may include a functional group including a carboxyl group (—COOH) and a hydroxyl group (—OH). The sensitive material SM may adsorb or desorb the target gas through the functional group. When the graphene is used as the sensitive material SM, the adsorption/desorption performance of the target gas may be improved by π-bonding of the functional group and the graphene. As a result, the response speed and recovery speed of the gas sensor, which will be described below, may be improved.

When the sensitive material SM adsorbs or desorbs the target gas, a capacitance of the capacitive gas sensor may be changed. Accordingly, the capacitive gas sensor may sense the target gas by measuring a change in capacitance. In addition, in order for the capacitive gas sensor to easily measure the change in capacitance, the porous structure 100 may be made of a material having a low dielectric constant.

In the capacitive gas sensor, a frequency of a voltage applied to the upper electrode 200 and the lower electrode 300 may be differently controlled according to a type of the target gas (for example, any one of a methanol gas, a toluene gas, and an acetone gas). In addition, the capacitive gas sensor may selectively sense any one of a methanol gas, a toluene gas, and an acetone gas according to a frequency of the voltage applied to the upper electrode 200 and the lower electrode 300.

For example, when the frequency of the voltage applied to the upper electrode 200 and the lower electrode 300 is 10 KHz or greater and 1 MHz or less, the capacitive gas sensor may sense the methanol gas. Alternatively, as another example, when the frequency of the voltage applied to the upper electrode 200 and the lower electrode 300 is greater than 800 Hz and less than 3,000 Hz, the capacitive gas sensor may sense the toluene gas. Alternatively, as still another example, when the frequency of the voltage applied to the upper electrode 200 and the lower electrode 300 is greater than 300 Hz and less than 800 Hz, the capacitive gas sensor may sense the acetone gas.

That is, according to one embodiment of the present invention, the capacitive gas sensor may include: the sensitive material SM for adsorbing or desorbing the target gas (for example, a volatile organic compounds gas such as a methanol gas, a toluene gas, and an acetone gas); the upper electrode 200 surrounding the sensitive material SM; a lower electrode 300 facing the upper electrode 200; and the porous structure 100 (for example, anodic aluminum oxide) disposed between the upper electrode 200 and the lower electrode 300, wherein a capacitance changes as the sensitive material adsorbs or desorbs the target gas. Accordingly, it is possible to provide a capacitive gas sensor with improved response speed and recovery speed.

Hereinabove, the capacitive gas sensor and the method for manufacturing the same according to the embodiment of the present invention have been described. Hereinafter, specific experimental examples and characteristic evaluation results of the capacitive gas sensor and the method for manufacturing the same according to the embodiment of the present invention will be described.

Manufacture of Capacitive Gas Sensor According to Example 1

An anodic aluminum oxide template having a diameter of 25 mm and a pore size of 200 nm was prepared. A ring-shaped gold (Au) upper electrode was formed on an upper surface of the prepared porous anodic aluminum oxide, and a circle plate-shaped gold (Au) lower electrode was formed on a lower surface thereof. Thereafter, the porous anodic aluminum oxide template was placed on a hot plate of 60° C., and a source solution having a 0.5 ml dose, in which graphene having a concentration of 1.6 wt % and ethanol were mixed, was provided to an exposed region of the upper surface of the porous anodic aluminum oxide, thereby manufacturing a capacitive gas sensor according to Example 1.

Manufacture of Capacitive Gas Sensor According to Example 2

The capacitive gas sensor according to Example 1 described above was manufactured, but a porous anodic aluminum oxide template having a diameter of 50 mm was used.

Manufacture of Capacitive Gas Sensor According to Comparative Example

An anodic aluminum oxide template having a diameter of 25 mm and a pore size of 200 nm was prepared. A first electrode of graphene gold (Au) and a second electrode of gold (Au), which were spaced apart from each other in a horizontal direction, were formed on the upper surface of the porous anodic aluminum oxide template, thereby manufacturing a capacitive gas sensor according to Comparative Example.

The characteristics of the capacitive gas sensors according to the above-described Examples and Comparative Example are summarized through <Table 1> below.

TABLE 1

| Classification | Electrode Structure | Diameter Size |
|---|---|---|
| Example 1 | Upper Electrode-Lower Electrode Vertical Structure | 25 mm |

TABLE 1-continued

| Classification | Electrode Structure | Diameter Size |
|---|---|---|
| Example 2 | Upper Electrode-Lower Electrode Vertical Structure | 50 mm |
| Comparative Example | First Electrode-Second Electrode Horizontal Structure | 25 mm |

Figure 6:
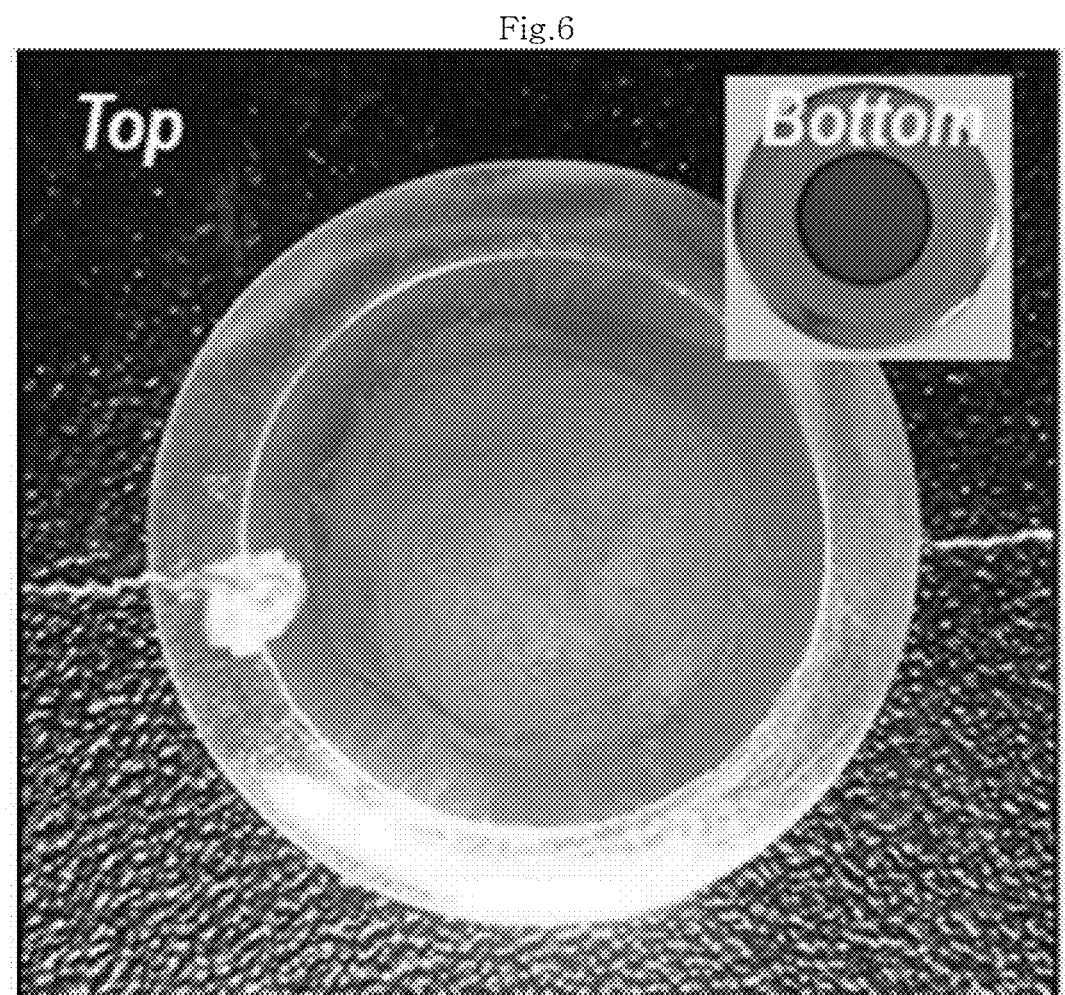
FIG. 6 is an image of the capacitive gas sensor according to the embodiment of the present invention.

FIG. 6 is an image of the capacitive gas sensor according to the embodiment of the present invention.

Referring to FIG. 6, the capacitive gas sensor according to Example 1 was photographed and shown. As can be seen in FIG. 6, it was confirmed that the upper electrode (Top) of the capacitive gas sensor according to the embodiment has a ring shape, and the lower electrode (Bottom) thereof has a circular plate shape.

Figure 7:
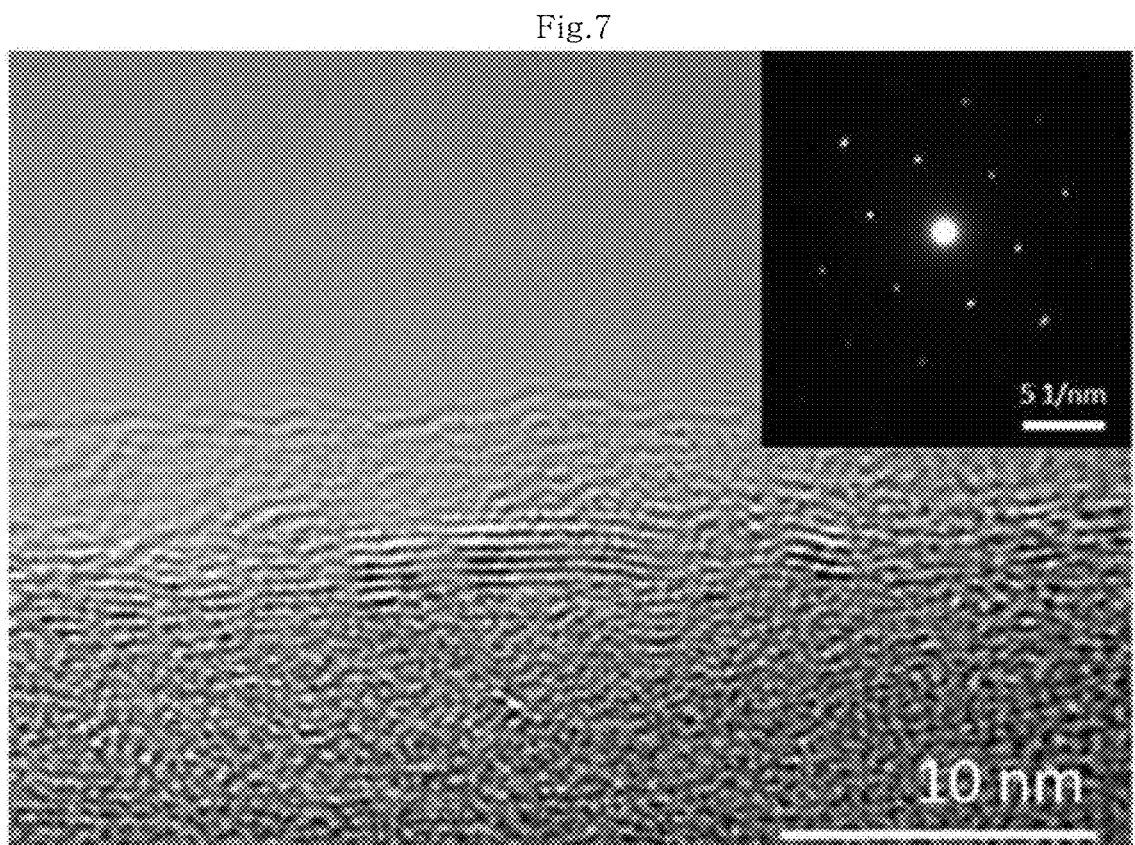
FIG. 7 is an image of the upper electrode included in the capacitive gas sensor according to the embodiment of the present invention.

FIG. 7 is an image of the sensitive material included in the capacitive gas sensor according to the embodiment of the present invention.

Referring to FIG. 7, a transmission electron microscope (TEM) image of the sensitive material included in the capacitive gas sensor according to Example 1 was shown. As can be seen in FIG. 7, it was confirmed that the sensitive material included in the capacitive gas sensor has a layered structure of about 6 layers of graphene having a thickness of several nanometers.

Figure 8:
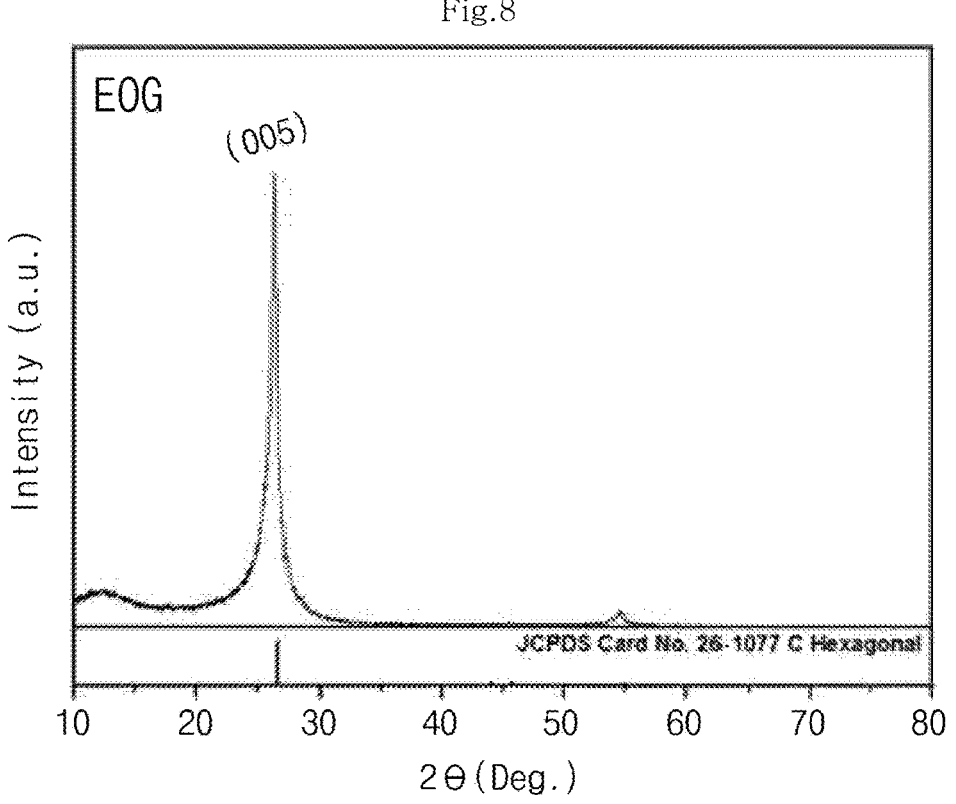
FIG. 8 is a graph showing analysis of a structure of the upper electrode included in the capacitive gas sensor according to the embodiment of the present invention.

FIG. 8 is a graph showing analysis of a structure of the sensitive material included in the capacitive gas sensor according to the embodiment of the present invention.

Referring to FIG. 8, X-ray diffraction (XRD) analysis results of the sensitive material included in the capacitive gas sensor according to Example 1 were shown. As can be seen in FIG. 8, it was confirmed that the sensitive material included in the capacitive gas sensor has a carbon (JCPDS No. 26-1077) phase with a hexagonal structure. In addition, as no other peak related to carbon was observed, it could be found that the sensitive material is made of high-purity graphene.

Figure 9:
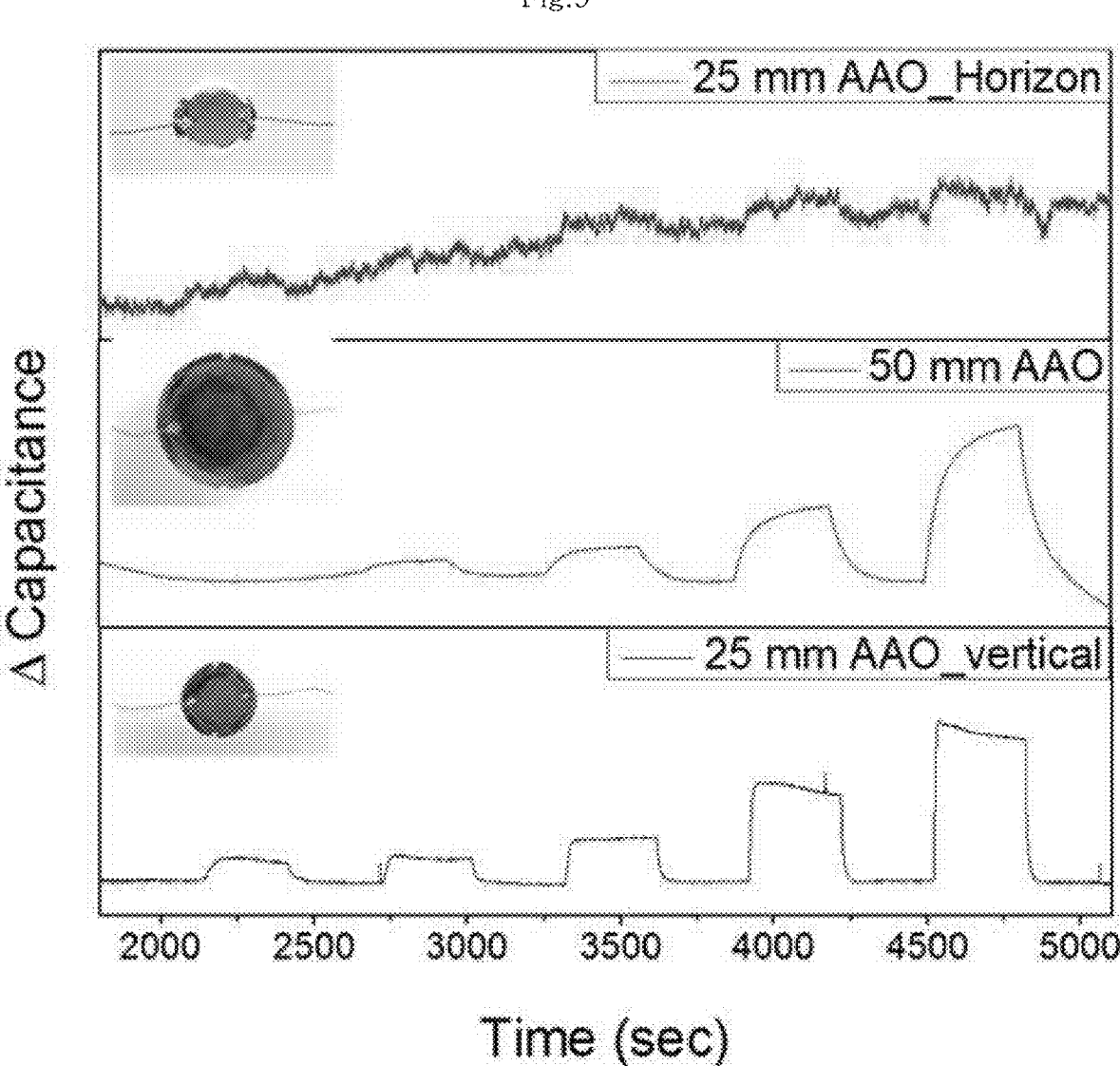
FIG. 9 is a graph showing a comparison between electrical characteristics of capacitive gas sensors according to Examples and Comparative Example.

FIG. 9 is a graph showing a comparison between electrical characteristics of capacitive gas sensors according to Examples and Comparative Example.

Referring to FIG. 9, after a capacitive gas sensor (25 mm, AAO_vertical) according to Example 1, a capacitive gas sensor (50 mm, AAO) according to Example 2, and a capacitive gas sensor (25 mm, AAO_Horizon) according to Comparative Example were prepared, methanol gases having concentrations of 5, 10, 20, 50, and 100 ppm were supplied to gas sensors, respectively, and a change in capacitance over time was shown.

As can be seen in FIG. 9, it was confirmed that the capacitive gas sensor according to Comparative Example generates large signal to noise, so that the capacitance is not substantially changed according to the gas concentration and adsorption/desorption of the methanol gas. On the other hand, it could be confirmed that the capacitive gas sensors according to Examples 1 and 2 have reduced noise due to a phase difference between the vertical structures of the upper electrode and the lower electrode, so that the capacitance is changed according to the gas concentration and adsorption/desorption of the methanol gas. In particular, it could be confirmed that the capacitive gas sensor according to Example 1 has a remarkably fast response speed and recovery speed according to the adsorption/desorption as compared to the capacitive gas sensor according to Example 2.

Accordingly, it can be seen that sensing characteristics of the gas sensor may be improved due to the vertical structures of the upper electrode and the lower electrode. In addition, it can be seen that the sensing characteristics of the gas sensor may be improved by controlling the diameter of the porous anodic aluminum oxide to 25 mm.

Figure 10:
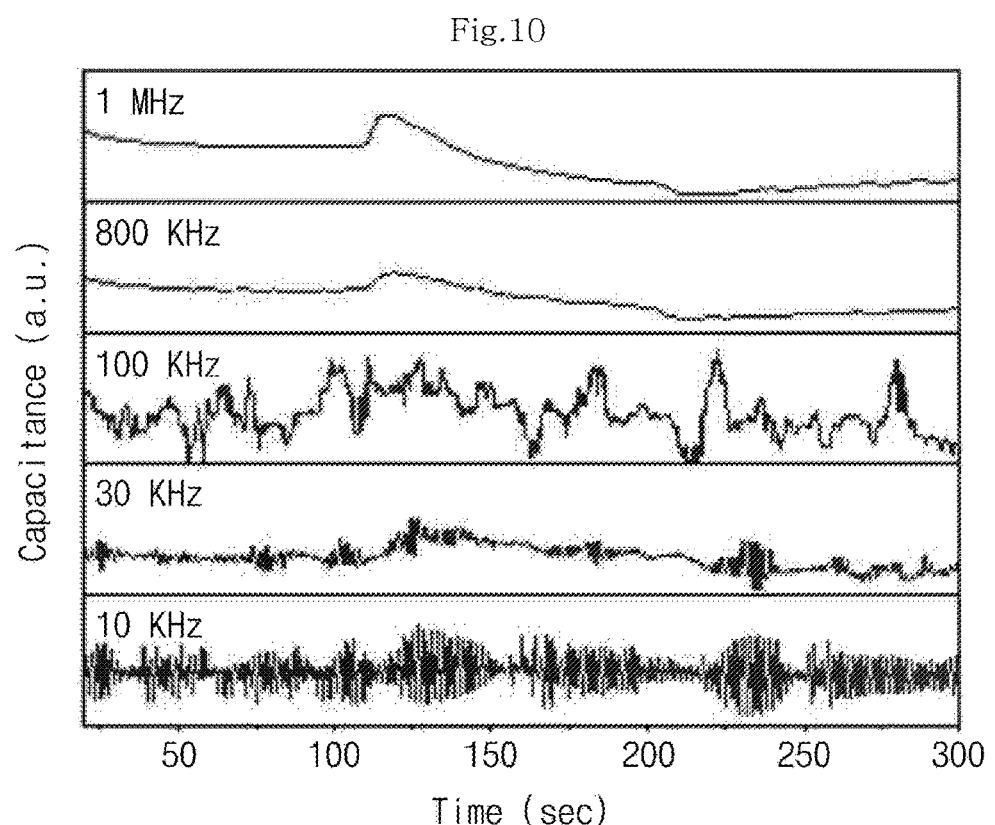
FIGS. 10 and 11 are graphs showing methanol gas sensing characteristics of the capacitive gas sensor according to the embodiment of the present invention.
Figure 11:
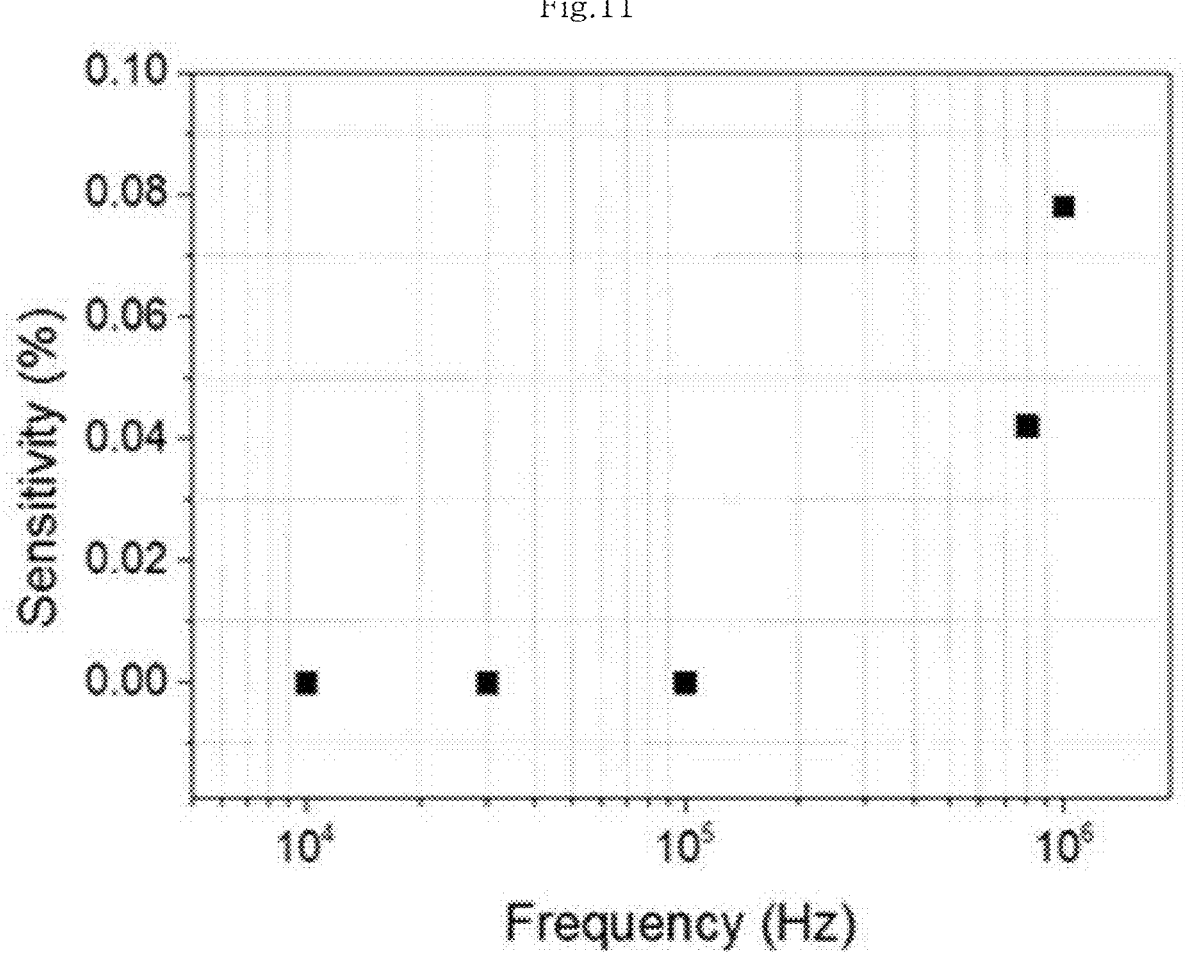

FIGS. 10 and 11 are graphs showing methanol gas sensing characteristics of the capacitive gas sensor according to the embodiment of the present invention.

Referring to FIGS. 10 and 11, a dry air gas was supplied into the capacitive gas sensor according to Example 1 for 100 seconds to stabilize the capacitive gas sensor, the methanol gas having a concentration of 100 ppm was supplied and adsorbed for 100 seconds, and then the dry air gas was supplied into the capacitive gas sensor again for 100 seconds to desorb the methanol gas. FIG. 10 shows a rate of change in capacitance (a.u.) according to the change in frequency of the voltage, which is applied to the upper electrode and the lower electrode, to 10 KHz, 30 KHz, 100 KHz, 800 KHz, and 1 MHz under the above-described experimental conditions, and FIG. 11 shows sensitivity (%) according to the change in frequency of the voltage applied to the upper electrode and the lower electrode under the above-described experimental conditions. In addition, the magnitude of the voltage applied to the upper electrode and the lower electrode is 1 V.

As can be seen in FIGS. 10 and 11, it was confirmed that the capacitive gas sensor according to Example 1 may sense the methanol gas in a frequency range of 10 kHz or greater and 1 MHz or less. In particular, when the frequency of the voltage applied to the upper electrode and the lower electrode is 1 MHz, it could be confirmed that the sensing sensitivity of the methanol gas is the highest.

Figure 12:
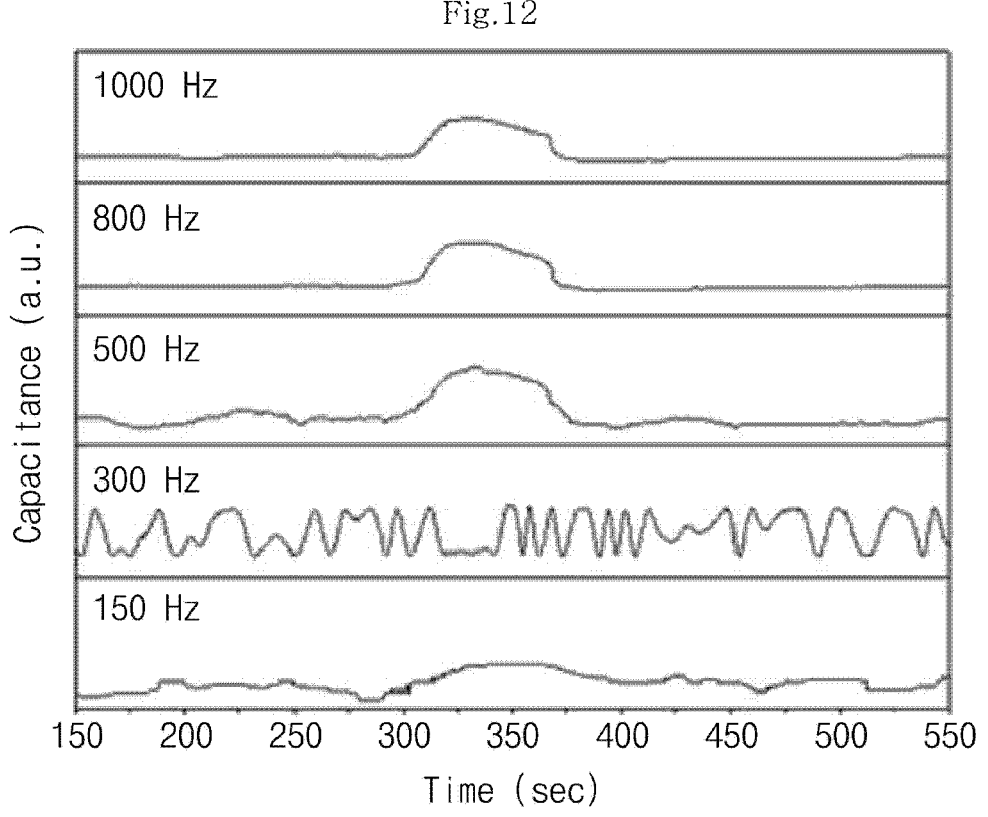
FIGS. 12 and 13 are graphs showing toluene gas sensing characteristics of the capacitive gas sensor according to the embodiment of the present invention.
Figure 13:
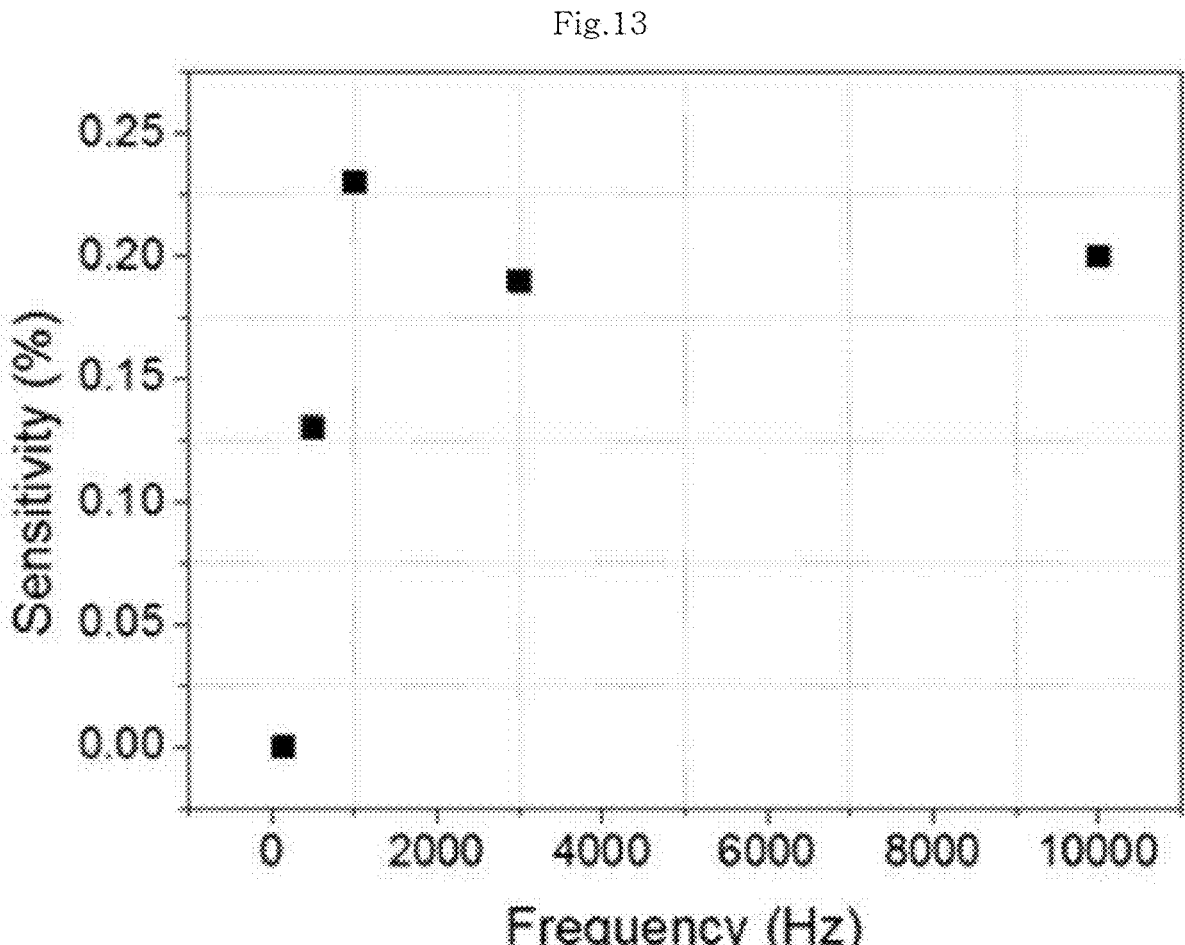

FIGS. 12 and 13 are graphs showing toluene gas sensing characteristics of the capacitive gas sensor according to the embodiment of the present invention.

Referring to FIGS. 12 and 13, the dry air gas was supplied into the capacitive gas sensor according to Example 1 for 300 seconds to stabilize the capacitive gas sensor, the toluene gas having a concentration of 100 ppm was supplied and adsorbed for 300 seconds, and then the dry air gas was supplied into the capacitive gas sensor again for 300 seconds to desorb the toluene gas. FIG. 12 shows a rate of change in capacitance (a.u.) according to the change in frequency of the voltage, which is applied to the upper electrode and the lower electrode, to 150 Hz, 500 Hz, 1,000 Hz, 3,000 Hz, and 10,000 Hz under the above-described experimental conditions, and FIG. 13 shows sensitivity (%) according to the change in frequency of the voltage applied to the upper electrode and the lower electrode under the above-described experimental conditions. In addition, the magnitude of the voltage applied to the upper electrode and the lower electrode is 1 V.

As can be seen in FIGS. 12 and 13, it was confirmed that the capacitive gas sensor according to Example 1 has increased capacitance as the frequency of the voltage applied to the upper electrode and the lower electrode increases from 800 Hz to 1,000 Hz, but has reduced capacitance as the frequency of the voltage of the upper electrode and the lower electrode increases from 1,000 Hz to 3,000 Hz starting from 1,000 Hz. Accordingly, it can be seen that the sensing sensitivity for the toluene gas may be improved as the frequency of the voltage applied to the upper electrode and the lower electrode of the capacitive gas sensor according to the embodiment is controlled to be greater than 800 Hz and less than 3,000 Hz.

Figure 14:
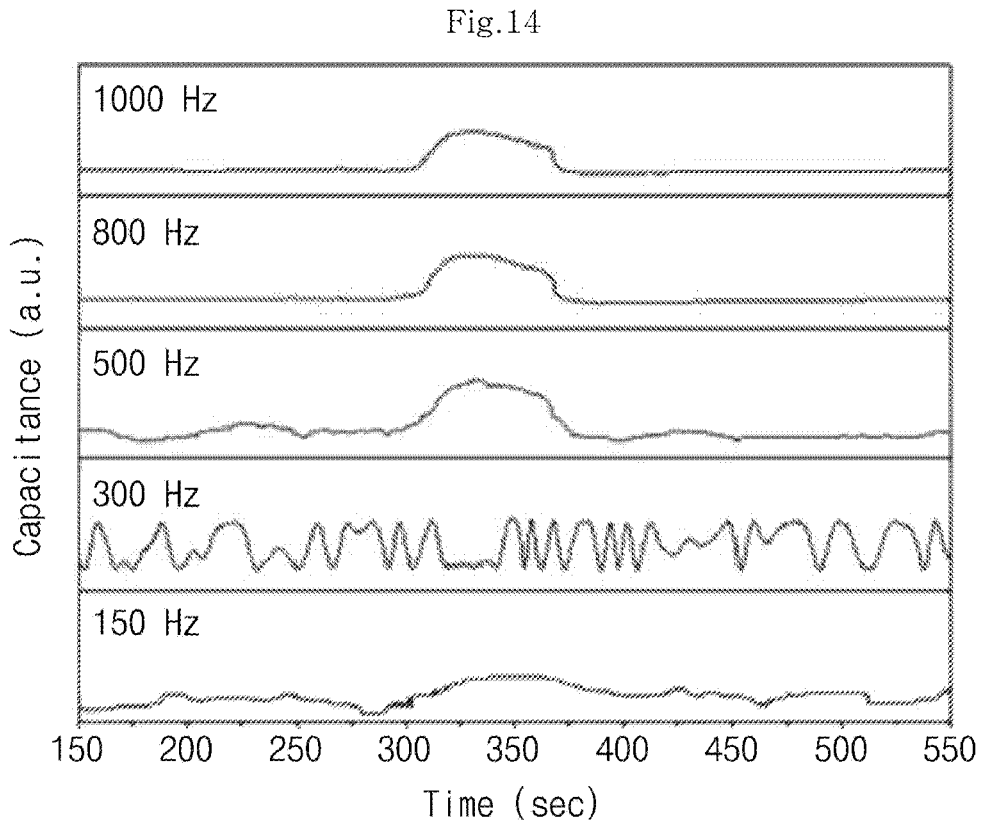
FIGS. 14 and 15 are graphs showing acetone gas sensing characteristics of the capacitive gas sensor according to the embodiment of the present invention.
Figure 15:
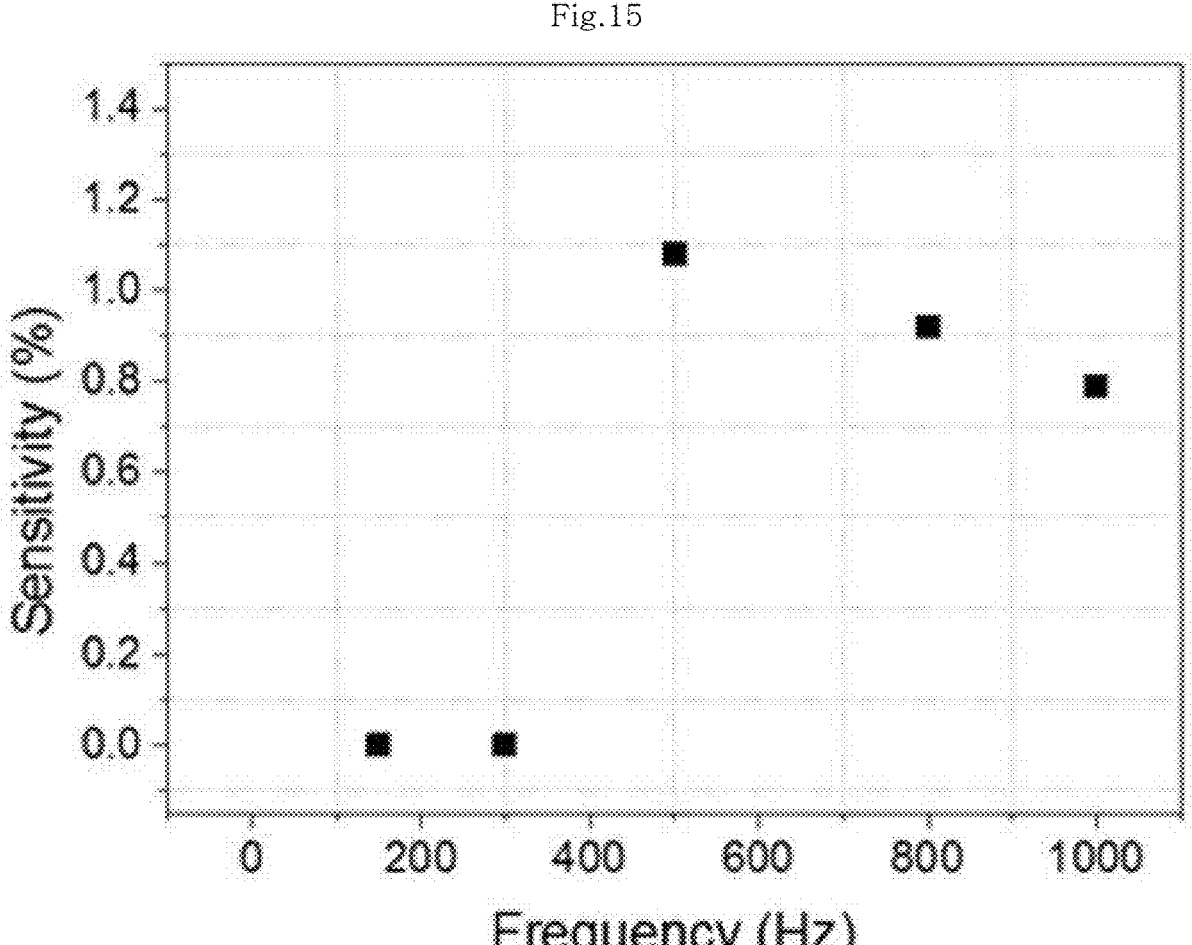

FIGS. 14 and 15 are graphs showing acetone gas sensing characteristics of the capacitive gas sensor according to the embodiment of the present invention.

Referring to FIGS. 14 and 15, the dry air gas was supplied into the capacitive gas sensor according to Example 1 for 300 seconds to stabilize the dry air gas, the acetone gas having a concentration of 100 ppm was supplied and adsorbed for 60 seconds, and then the dry air gas was supplied into the capacitive gas sensor again for 300 seconds to desorb the acetone gas. FIG. 14 shows a rate of change in capacitance (a.u.) according to the change in frequency of the voltage, which is applied to the upper electrode and the lower electrode, to 150 Hz, 300 Hz, 500 Hz, 800 Hz, and 1,000 Hz under the above-described experimental conditions, and FIG. 15 shows sensitivity (%) according to the change in frequency of the voltage applied to the upper electrode and the lower electrode under the above-described experimental conditions. In addition, the magnitude of the voltage applied to the upper electrode and the lower electrode is 1 V.

As can be seen in FIGS. 14 and 15, it was confirmed that the capacitive gas sensor according to Example 1 has increased capacitance as the frequency of the voltage applied to the upper electrode and the lower electrode increases from 300 Hz to 500 Hz, but has reduced capacitance as the frequency of the voltage of the upper electrode and the lower electrode increases from 500 Hz to 800 Hz starting from 500 Hz. Accordingly, it can be seen that the sensing sensitivity for the acetone gas may be improved as the frequency of the voltage applied to the upper electrode and the lower electrode of the capacitive gas sensor according to the embodiment is controlled to be greater than 300 Hz and less than 800 Hz.

As can be seen in FIGS. 10 to 15, it can be seen that the capacitive gas sensor according to the embodiment of the present invention may selectively sense any one of the methanol gas, the toluene gas, and the acetone gas according to the frequency of the voltage applied to the upper electrode and the lower electrode.

In addition to the sensing of the methanol gas, the toluene gas, and the acetone gas described above, in order to confirm the sensing characteristics of the volatile organic compound, the volatile organic compound was supplied into the capacitive gas sensor according to the embodiment at concentrations of 5 ppm, 10 ppm, 20 ppm, 50 ppm, and 100 ppm, and change in capacitance of the capacitive gas sensor was measured by LCR meter analysis. It can be seen that in the capacitive gas sensor according to the embodiment, the capacitance for the volatile organic compound was changed, thereby easily sensing the volatile organic compound. More specific experimental conditions are summarized in <Table 2> below.

TABLE 2

| VOCs MFC (500 ppm) | Air MFC (99.99%) | Concentration (ppm) |
|---|---|---|
| 5 | 495 | 5 |
| 10 | 490 | 10 |
| 20 | 480 | 20 |
| 50 | 450 | 50 |
| 100 | 400 | 100 |

Figure 16:
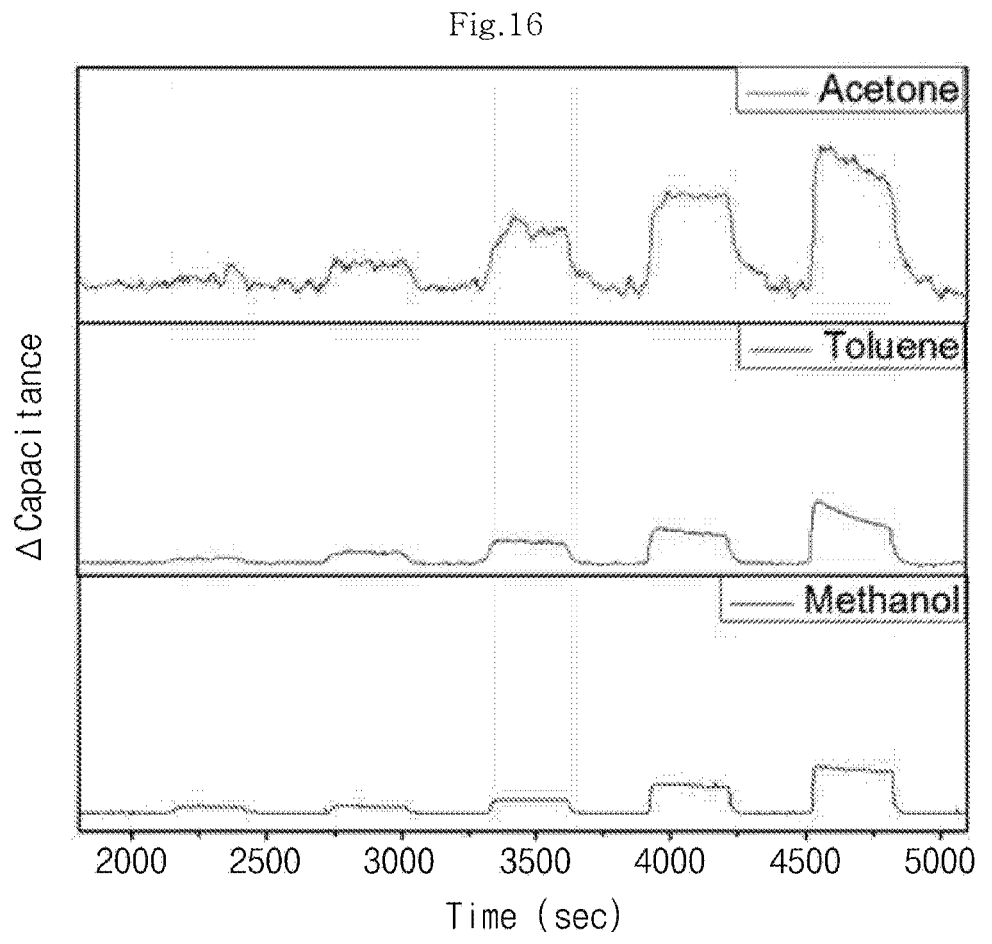

FIG. 16 is a graph showing a comparison between sensing characteristics for a type of a target gas of the capacitive gas sensor according to the embodiment of the present invention.

Referring to FIG. 16, after the methanol gas, the toluene gas, and the acetone gas were supplied into the capacitive gas sensor according to Example 1, change in capacitance over time was shown. More specifically, the methanol gas was measured under the condition that the frequency of the voltage applied to the upper electrode and the lower electrode is 1 MHz, the toluene gas was measured under the condition that the frequency is 1,000 Hz, and the acetone gas was measured under the condition that the frequency is 500 Hz. In addition, the time (sec) shown in FIG. 16 means a time to supply the gas, and as the time increases, the gas concentration also increases.

As can be seen in FIG. 16, it was confirmed that the capacitance of the capacitive gas sensor according to Example 1 is changed according to adsorption of the methanol gas, the toluene gas, and the acetone gas, and the sensing sensitivity is increased as the gas concentration is increased.

Figure 17:
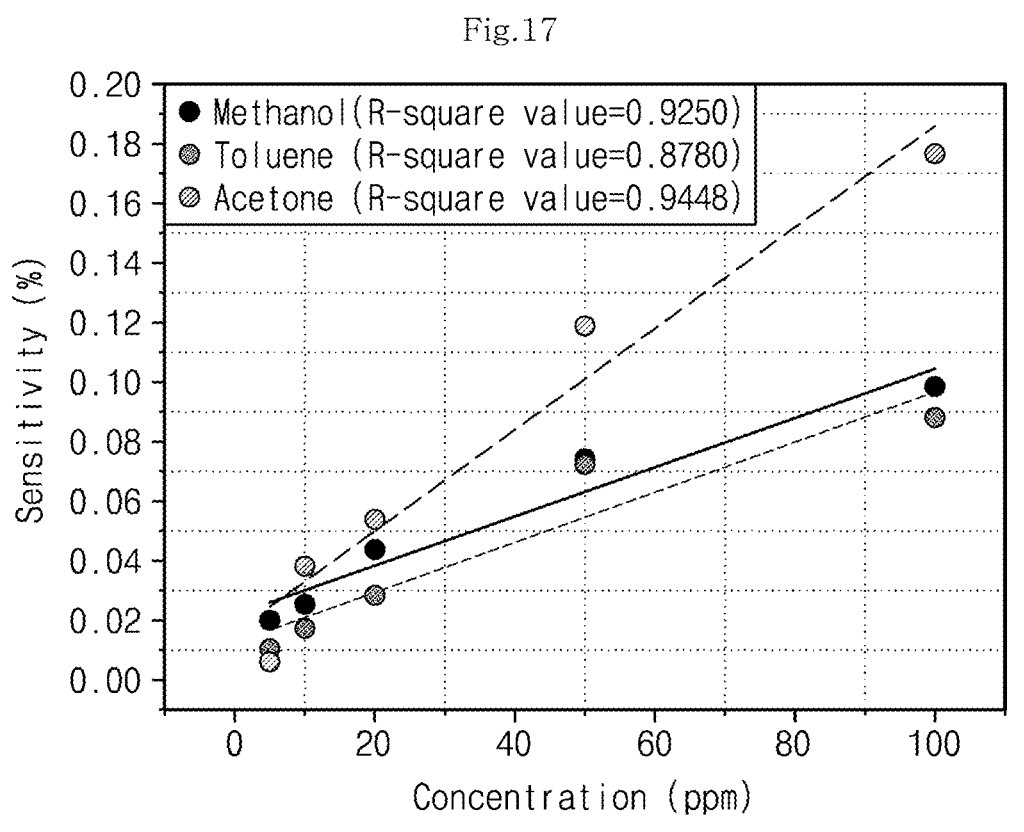
Figure 18:
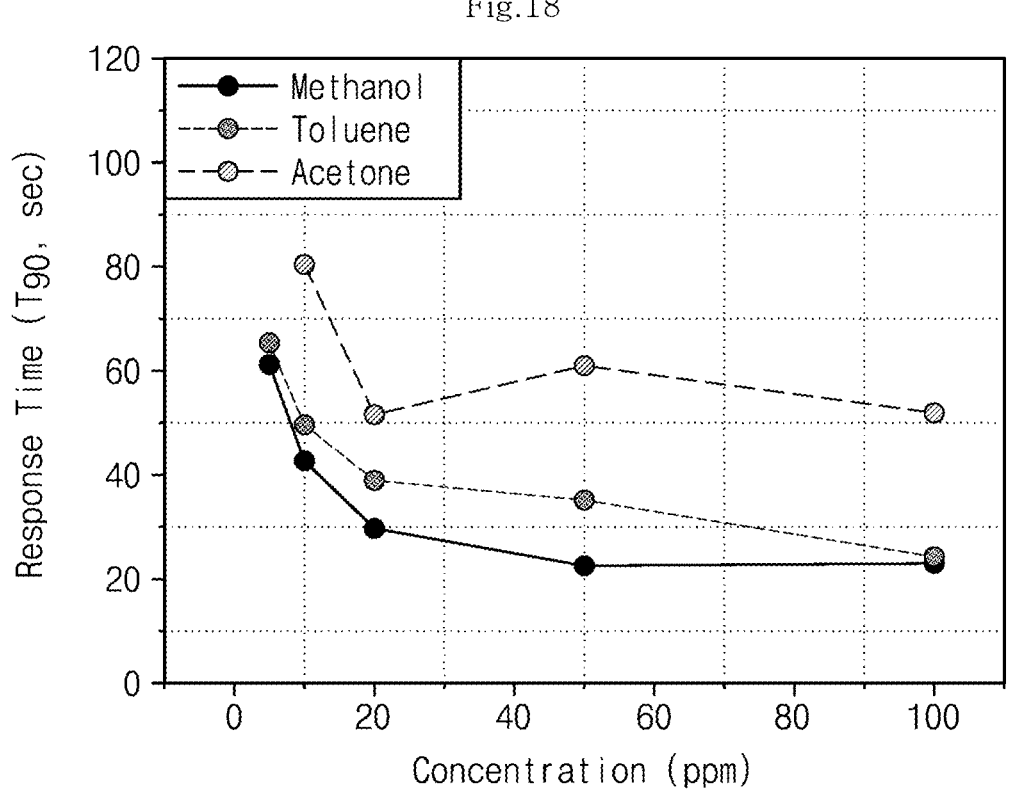
FIG. 18 is a graph showing a response time according to the concentrations of gases provided to the capacitive gas sensor according to the embodiment of the present invention.
Figure 19:
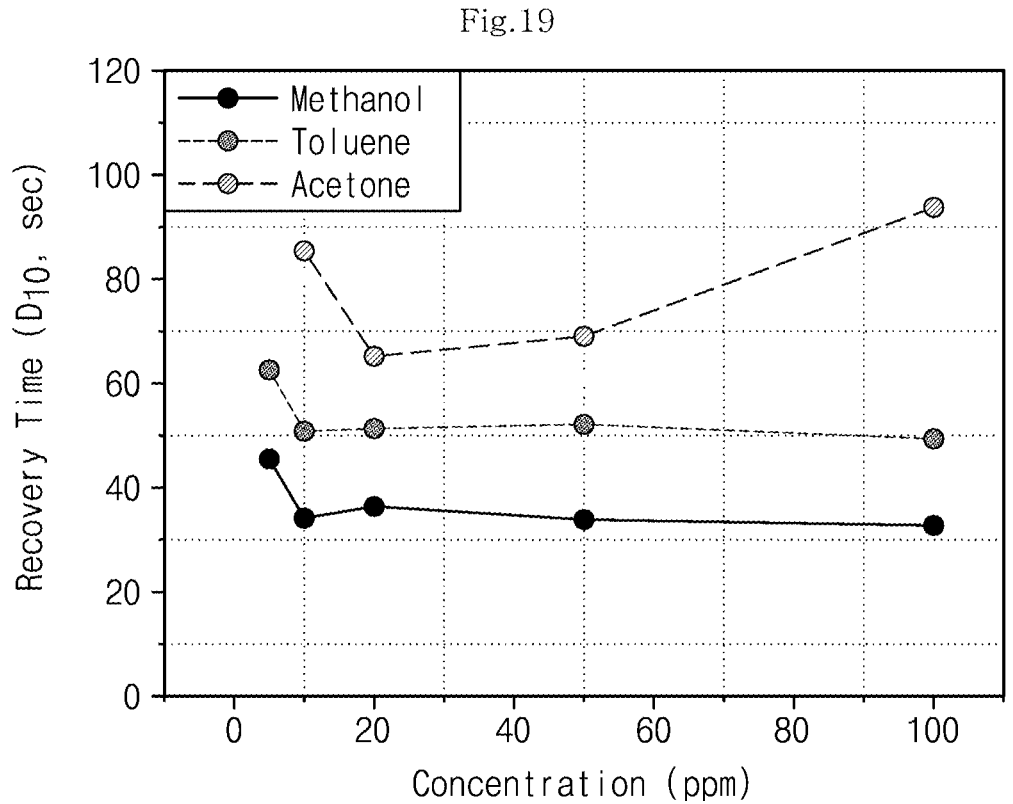
FIG. 19 is a graph showing a recovery time according to the concentrations of gases provided to the capacitive gas sensor according to the embodiment of the present invention.

FIG. 17 is a graph showing sensitivity according to concentrations of gases provided to the capacitive gas sensor according to the embodiment of the present invention, FIG. 18 is a graph showing a response time according to the concentrations of gases provided to the capacitive gas sensor according to the embodiment of the present invention, and FIG. 19 is a graph showing a recovery time according to the concentrations of gases provided to the capacitive gas sensor according to the embodiment of the present invention.

Referring to FIGS. 17 to 19, the methanol gas, the toluene gas, and the acetone gas were supplied into the capacitive gas sensor according to Example 1, and sensitivity (%), a response time $T_{90}$ (sec), and a recovery time $D_{10}$ (sec) were shown according to a gas concentration of each of the methanol gas, the toluene gas, and the acetone gas. The measurement results of FIGS. 17 to 19 are summarized through <Table 3> to <Table 5> below.

TABLE 3

| | Methanol | | | | |
| --- | --- | --- | --- | --- | --- |
| | 5 ppm | 10 ppm | 20 ppm | 50 ppm | 100 ppm |
| Sensitivity (%) | 0.020 | 0.025 | 0.043 | 0.074 | 0.098 |
| Response Time (sec) | 61.4 | 43.0 | 30.0 | 22.8 | 23.4 |
| Recovery Time (sec) | 45.6 | 34.2 | 36.4 | 33.8 | 32.8 |

TABLE 4

| | Toluene | | | | |
| --- | --- | --- | --- | --- | --- |
| | 5 ppm | 10 ppm | 20 ppm | 50 ppm | 100 ppm |
| Sensitivity (%) | 0.010 | 0.017 | 0.028 | 0.072 | 0.088 |
| Response Time (sec) | 65.6 | 49.8 | 39.2 | 35.4 | 24.8 |
| Recovery Time (sec) | 62.6 | 50.8 | 51.4 | 52.2 | 49.4 |

TABLE 5

| | Acetone | | | | |
| --- | --- | --- | --- | --- | --- |
| | 5 ppm | 10 ppm | 20 ppm | 50 ppm | 100 ppm |
| Sensitivity (%) | — | 0.038 | 0.054 | 0.118 | 0.177 |
| Response Time (sec) | — | 80.6 | 52 | 61.5 | 52.2 |

TABLE 5-continued

| | Acetone | | | | |
| --- | --- | --- | --- | --- | --- |
| | 5 ppm | 10 ppm | 20 ppm | 50 ppm | 100 ppm |
| Recovery Time (sec) | — | 85.6 | 65.2 | 69.2 | 93.8 |

As can be seen in FIGS. 17 to 19 and <Table 3> to <Table 5>, it was confirmed that the capacitive gas sensor according to Example 1 shows a high R-square value of 0.87 or greater for all of the methanol gas, the toluene gas, and the acetone gas. In addition, it could be confirmed that the capacitive gas sensor according to Example 1 has rapid response time and recovery time within 100 seconds for all of the methanol gas, the toluene gas, and the acetone gas.

Since the kinetic diameter of the methanol gas is 3.80, the kinetic diameter of the toluene gas is 5.80, and the kinetic diameter of the acetone gas is 4.70, the methanol gas is rapidly adsorbed or desorbed as compared to other gases. Further, toluene has $\pi$-bonding in a carbon lattice due to $sp^2$ bonding of graphene, and the adsorption/desorption with weak bonding is achieved by the $\pi$-bonding, and thus there is a difference in adsorption/desorption characteristics as compared to the methanol gas.

Figure 20:
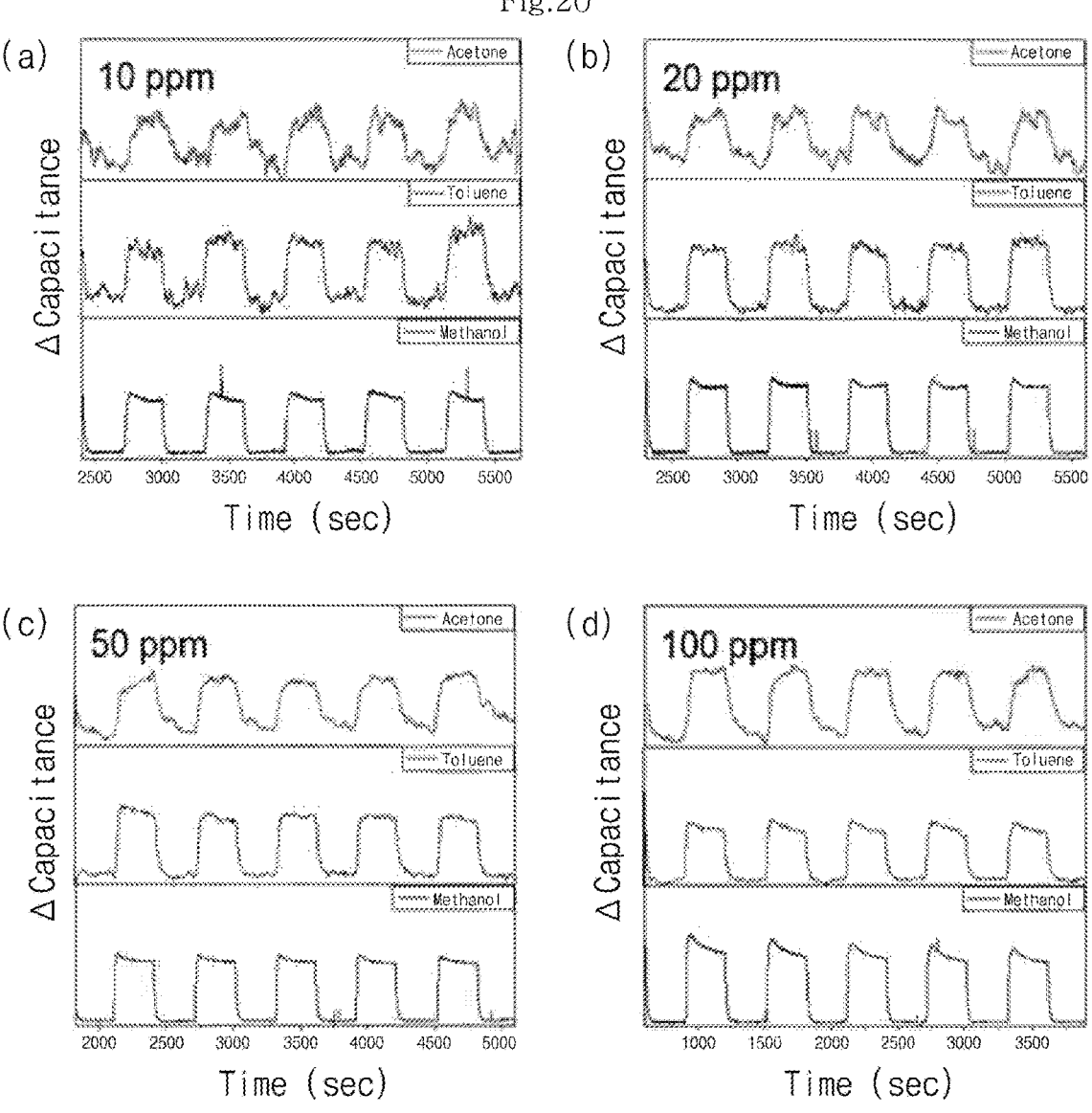
FIG. 20 is a graph showing reliability evaluation of the capacitive gas sensor according to the embodiment of the present invention.

FIG. 20 is a graph showing reliability evaluation of the capacitive gas sensor according to the embodiment of the present invention.

Referring to (a) to (d) of FIG. 20, reliability of the capacitive gas sensor according to Example 1 was evaluated by measuring change in capacitance ($\Delta$Capacitance) over time (sec) after the acetone gas, the toluene gas, and the methanol gas were injected repeatedly 5 times at concentrations of 10 ppm, 20 ppm, 50 ppm, and 100 ppm into the capacitive gas sensor according to Example 1. The reliability evaluation described above was performed at room temperature.

As can be seen from (a) to (d) of FIG. 20, it was confirmed that the capacitive gas sensor according to Example 1 has high reproducibility with precision of 1 or less during a plurality of repeated measurement processes. That is, it could be confirmed that the capacitive gas sensor according to Example 1 has high reliability in an environment at room temperature with respect to the sensing of the acetone gas, the toluene gas, and the methanol gas. In addition, it could be seen that even when the acetone gas, the toluene gas, and the methanol gas are repeatedly leaked, excellent sensing is performed at a low concentration.

Figure 21:
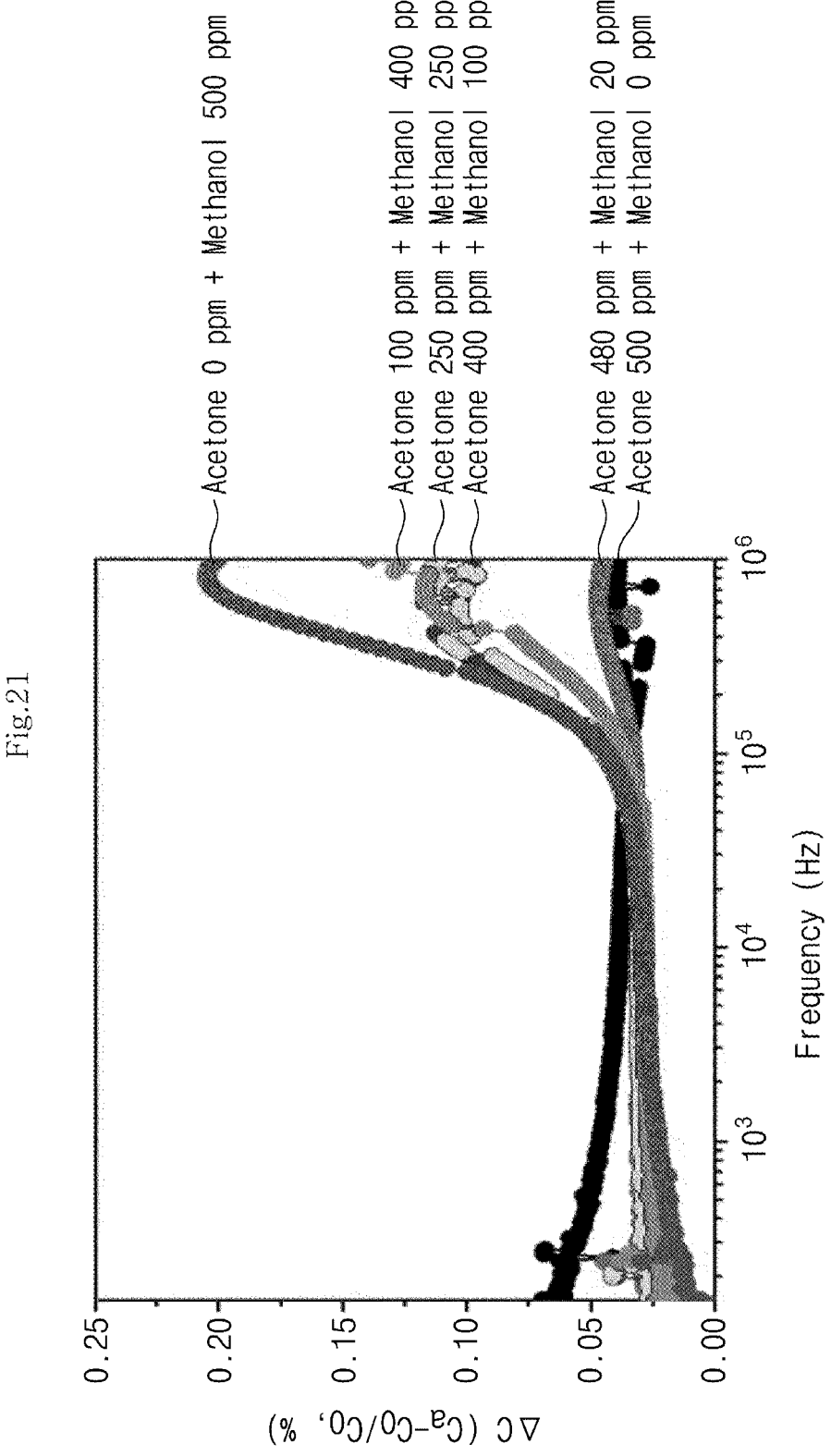
FIG. 21 is a graph showing a gas discrimination performance of the capacitive gas sensor according to the embodiment of the present invention.

FIG. 21 is a graph showing a gas discrimination performance of the capacitive gas sensor according to the embodiment of the present invention.

Referring to FIG. 21, the acetone gas and the methanol gas were simultaneously injected into the capacitive gas sensor according to Example 1, and then sensitivity ($\Delta C/C_0$, %) of the acetone gas injected into the capacitive gas sensor and sensitivity ($\Delta C/C_0$, %) of the methanol gas injected into the capacitive gas sensor were measured according to a change in frequency (Hz). The acetone gas and the methanol gas were injected at different concentrations, and the concentrations of the injected acetone gas and methanol gas are shown in <Table 6> below. In addition, the results measured at a frequency of 500 Hz are summarized through <Table 7> below.

TABLE 6

| Acetone MFC Concentration (ppm) | Methanol MFC Concentration (ppm) |
|---|---|
| 500 | 0 |
| 480 | 20 |
| 400 | 100 |
| 250 | 250 |
| 100 | 400 |
| 0 | 500 |

TABLE 7

| Concentration (Methanol Gas Concentration, ppm) | Acetone Sensitivity ($\Delta C/C_0$, %) | Methanol Sensitivity ($\Delta C/C_0$, %) |
|---|---|---|
| 0 | 0.178 | 0.000 |
| 20 | 0.103 | 0.070 |
| 100 | 0.100 | 0.097 |
| 250 | 0.039 | 0.111 |
| 400 | 0.034 | 0.140 |
| 500 | 0.039 | 0.200 |

As can be seen in FIG. 21 and <Table 7>, it was confirmed that as the concentration of the acetone gas at a frequency of 500 Hz decreases from 500 ppm to 0 ppm, the sensitivity of the acetone gas decreases from 0.178% to 0.039%, whereas the sensitivity of the methanol gas increases from 0% to 0.2%.

That is, when the acetone gas and the methanol gas are simultaneously injected, since frequency regions having the highest sensitivity characteristics due to resonance of the acetone gas and the methanol gas are significantly different from each other (acetone: 500 Hz, methanol: 1 MHz), it can be seen that there is no problem in simultaneously analyzing the acetone gas and the methanol gas because there is little influence of other gases on each sensitivity measurement.

As a result, when the acetone gas and the methanol gas are simultaneously injected, it can be confirmed that an increase in the sensitivity according to the increase of the gas concentration in each resonant frequency region is proportional, and it can be seen that excellent gas characteristics are selectively exhibited for each resonant frequency region.

While the present invention has been described in connection with the embodiments, it is not to be limited thereto but will be defined by the appended claims. In addition, it is to be understood that those skilled in the art can substitute, change or modify the embodiments in various forms without departing from the scope and spirit of the present invention.

INDUSTRIAL APPLICABILITY

The capacitive gas sensor and the method for manufacturing the same according to the embodiment of the present invention can be used in various fields required for sensing VOCs, such as health, environment, agriculture, national defense, and the like.

The invention claimed is:

1. A capacitive gas sensor comprising:
a sensitive material for adsorbing or desorbing a target gas;
an upper electrode surrounding the sensitive material;
a lower electrode facing the upper electrode; and
a porous structure disposed between the upper electrode and the lower electrode,
wherein a capacitance of the capacitive gas sensor changes as the sensitive material adsorbs or desorbs the target gas,
wherein the upper electrode has a ring shape with a hollow formed at a central portion thereof,
wherein the lower electrode has a circle plate shape,
wherein the sensitive material is disposed in the hollow formed at the central portion of the upper electrode, and
wherein the porous structure includes anodic aluminum oxide (AAO).

2. The capacitive gas sensor of claim 1, wherein a frequency of a voltage applied to the upper electrode and the lower electrode is differently controlled according to a type of the target gas.

3. The capacitive gas sensor of claim 2, wherein
the target gas includes a methanol gas, a toluene gas, or an acetone gas, and
the target gas is selectively sensed according to the frequency of the voltage applied to the upper electrode and the lower electrode.

4. The capacitive gas sensor of claim 3, wherein, when the frequency of the voltage applied to the upper electrode and the lower electrode is 10 kHz or greater and 1 MHz or less, the methanol gas is sensed.

5. The capacitive gas sensor of claim 3, wherein, when the frequency of the voltage applied to the upper electrode and the lower electrode is greater than 800 Hz and less than 3,000 Hz, the toluene gas is sensed.

6. The capacitive gas sensor of claim 3, wherein, when the frequency of the voltage applied to the upper electrode and the lower electrode is greater than 300 Hz and less than 800 Hz, the acetone gas is sensed.

7. The capacitive gas sensor of claim 1, wherein the sensitive material includes any one of graphene, carbon nanotube (CNT), amorphous carbon, active carbon, and biochar.

8. The capacitive gas sensor of claim 1, wherein
the sensitive material includes a functional group including a carboxyl group (—COOH) and a hydroxyl group (—OH), and
the target gas is adsorbed or desorbed by the functional group.

* * * * *